(12) United States Patent
Scott et al.

(10) Patent No.: US 6,770,294 B2
(45) Date of Patent: Aug. 3, 2004

(54) FISH GELATIN COMPOSITIONS CONTAINING A HYDROCOLLOID SETTING SYSTEM

(75) Inventors: Robert Scott, Sint Niklaas (BE); Dominque Cadé, Colmar (FR); Xiongwei He, Andolsheim (FR)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/804,093

(22) Filed: Mar. 12, 2001

(65) Prior Publication Data

US 2001/0024678 A1 Sep. 27, 2001

Related U.S. Application Data

(63) Continuation of application No. 09/220,933, filed on Dec. 24, 1998, now abandoned.

(30) Foreign Application Priority Data

Dec. 26, 1997 (FR) .............................. 97 16574

(51) Int. Cl.[7] .............................. A61K 9/64; A61K 9/48; A61K 9/62

(52) U.S. Cl. .................. 424/456; 424/451; 424/453; 424/454; 424/461; 424/463

(58) Field of Search .................... 424/451, 456, 424/453, 454, 461, 463

(56) References Cited

U.S. PATENT DOCUMENTS

| | | | | |
|---|---|---|---|---|
| 4,876,105 A | * | 10/1989 | Wolf et al. | |
| 4,892,766 A | * | 1/1990 | Jones | 428/36.4 |
| 5,603,952 A | * | 2/1997 | Soper | |
| 5,683,717 A | * | 11/1997 | Shen | |
| 5,756,123 A | * | 5/1998 | Yamamoto et al. | |
| 6,423,346 B1 | * | 7/2002 | Hansen et al. | 424/520 |

* cited by examiner

Primary Examiner—Thurman K. Page
Assistant Examiner—Humera N. Sheikh
(74) Attorney, Agent, or Firm—Evan J. Federman; Kenneth G. Lemke

(57) ABSTRACT

The invention concerns Gelatin compositions for the use in pharmaceutical, veterinary, food, cosmetic or other products like films for wrapping food, aspics or jellies, preferably for predosed formulations like soft or hard gelatin capsules wherein the gelatin used is of non-bovine and non-pig origin and preferably derived from fish, poultry or plant sources. Especially preferred are film compositions for hard gelatine capsules prepared from fish gelatin.

2 Claims, 1 Drawing Sheet

USP dissolution results

FISH GELATIN COMPOSITIONS CONTAINING A HYDROCOLLOID SETTING SYSTEM

RELATED APPLICATIONS

This application is a continuation application of U.S. Ser. No. 09/220,933 filed Dec. 24, 1998, now abandoned, which application claims benefit pursuant to 35 U.S.C. §119 (a)–(d) of prior foreign application filed Dec. 26, 1997 in France as application number 9716574 and PCT application number PCT/USS98/23484, filed Nov. 4, 1998.

FIELD OF THE INVENTION

The invention concerns gelatin compositions for the use in pharmaceutical, veterinary, food, cosmetic or other products like films for wrapping food, aspics or jellies, preferably for predosed formulations like soft or hard gelatin capsules wherein the gelatin used is of non-bovine and non-pig origin and preferably derived from fish, poultry or plant sources. Especially preferred are film compositions for hard gelatine capsules prepared from fish gelatin.

A second embodiment of the invention is the use of the film composition for the manufacturing of hard gelatin capsules by conventional dip moulding processes.

BACKGROUND OF THE INVENTION

The gelatin used for hard gelatin capsules is traditionally produced by extraction from collagen containing mammalian tissues, particularly such as pig skin and bovine bone. Gelatin from pig and bovine origin are preferably used for their gelling, film forming and surface-active properties. The manufacture of hard gelatin capsules by dip moulding process exploits fully its gelling and film forming abilities. Such capsules are manufactured by dipping mould pins into a hot solution of gelatin, removing the pins from the gelatin solution, allowing the gelatin solution attached on pins to set by cooling, drying and stripping the so-formed shells from the pins. The setting of the solution on the mould pins after dipping is the critical step to obtain an uniform thickness of the capsule shell.

Fish collagen is a further source of gelatin. However, it has long been known that gelatin derived from fish collagen lacks much of the gelling and setting ability of mammalian gelatins which limits the fish gelatin application. It is only applicable for products where a high viscosity of the solution without gel formation is desired, for example, in glue or food manufacturing. In the field of predosed pharmaceuticals, the fish gelatin can be used for microencapsulation (WO 9620612) or for the production of soft capsules where the gelling and setting ability is not a critical parameter in the manufacturing process.

A. N. Fraga et al. describe in J. Polym. Mater. 5 (1988) 49–55 the mechanical properties from fish Gelatins as a brittle behavior characteristic of a glassy material at normal temperatures. Such a brittleness is very undesired property for a gelatin capsule.

Norland Products Inc. describe in Research Disclosure 1987, 788 that water solutions of fish gelatin remain liquid down to 10° C., wheras water solutions of animal gelatin must be heated to temperatures over 30° C. to remain liquid. This behavior of fish gelatin will not allow the use in the conventional dip moulding process at conventional temperatures because of ist to low gelling temperature.

B. Leuenberger describes in Food Hydrocolloids 1991, 353–361 viscosity and gelation properties of different mammalian and fish gelatins with the conclusion that fish gelatin may be usefull in applications where high solution viscosity without gel formation is desired.

Surprisingly it has been found that fish gelatin can be used for the production of conventional Gelatins with conventional properties by adding a setting system to the aqueous fish gelatin solution.

SUMMARY OF THE INVENTION

The problem of the invention is therefore the provision of compositions for the production of Gelatins for the use in pharmaceutical, veterinary, food, cosmetic or other products like films for wrapping food, aspics or jellies, preferably for predosed formulations like soft or hard gelatin capsules wherein the gelatin used is of non-bovine and non-pig origin and preferably derived from fish, poultry or plant sources, and wherein a setting system is added to the aqueous gelatin solution. Especially preferred are film compositions for hard gelatine capsules prepared from fish gelatin.

Surprisingly this is achieved by the addition of a setting system and this allows the use of a wide range of gelatins from other sources than pigs or cattle for gelatin products for human consumption avoiding ethical and cultural problems.

BRIEF DESCRIPTION OF THE DRAWING

The sole FIGURE is a graph showing the percentage of acetaminophen dissolved from capsules produced in accordance with the present invention.

DETAILED DESCRIPTION OF THE INVENTION

Figure 1:
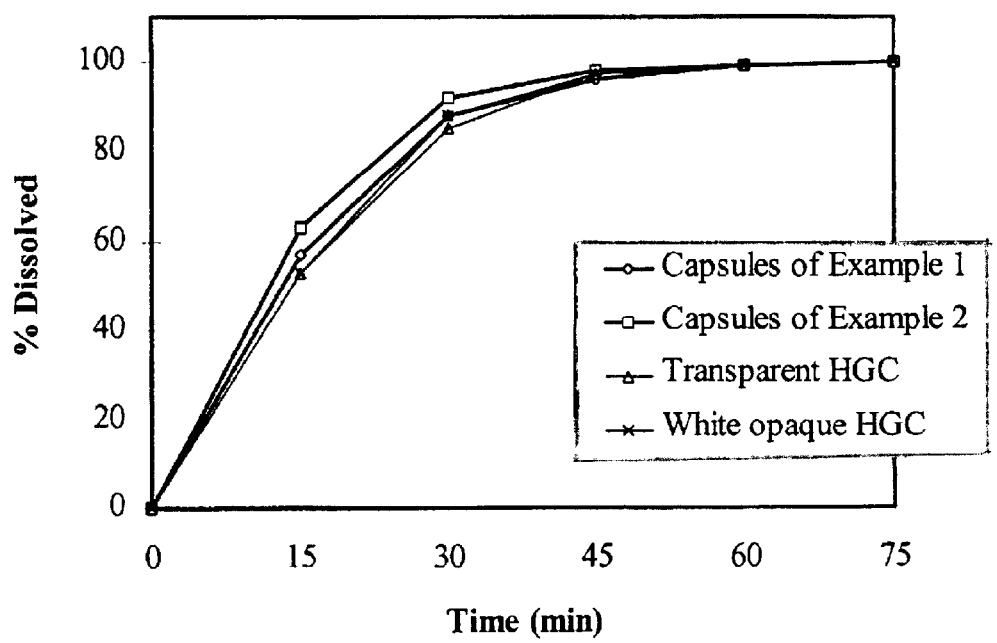

The addition of a setting system to the aqueous gelatin solution enables the adaption of specific and desired gelling properties also to gelatin solutions with normally insufficient gelling behavior, especially for the production of hard gelatin capsules. For the production of such capsules it is extremly important that the film forming gelation solution remaining on the mould pins after dipping is prohibited from flowing down the pins. Otherwise the obtained film will not have the desired uniform thickness.

Consequently hard gelatin capsules from other gelatin sources can be produced with the same equipment as for conventional hard gelatin capsules in the range of same process conditions. Furthermore capsules produced from compositions of the instant invention have the same dimensional specifications and allow the use of the existing filling machinery and do not require specific and new equipment for the capsule users. The capsules produced from the gelatin compositions of the invention have also acceptable mechanical and dissolution properties.

The gelatin concentration in the dipping solution is in a range of 10 to 60%, preferably in the range of 20 to 40% by weight.

The setting system consist of a hydrocolloid or mixtures of hydrocolloids and cations and may contain in addition sequestering agents.

Suitable hydrocolloides or mixtures producing synergistic properties may be selected from natural seaweeds, natural seed gums, natural plant exudates, natural fruit extracts, biosynthetic gums, bio-synthetic processed starch or cellulosic materials, preferred are the polysaccharides.

The preferred polysaccharides are alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, and other exocellular polysaccharides. Preferred are exocellular polysaccharides.

The preferred exocellular polysaccharides are xanthan, acetan, gellan, welan, rhamsan, furcelleran, succinoglycan, scleroglycan, schizophyllan, tamarind gum, curdlan, pullulan, dextran. Preferred are kappa-carrageenan or gellan gum or combinations like xanthan with locust bean gum or xanthan with konjac mannan. The amount of the hydrocolloid is preferably in the range of 0.01 to 5% by weight and especially preferred 0.03 to 1.0% in the aqueous gelatin solution.

The cations are preferably selected from, $K^+$, $Na^+$, $Li^+$, $NH_4^+$, $Ca^{++}$ or $Mg^{++}$, for kappa-carrageenan are preferred $K^+$, $NH_4^+$ or $Ca^{++}$.

The preferred sequestering agents are ethylenediaminetetraacetic acid, acetic acid, boric acid, citric acid, edetic acid, gluconic acid, lactic acid, phosphoric acid, tartaric acid or salts thereof, methaphosphates, dihydroxyethylglycine, lecithin or beta cyclodextrin and combinations thereof. Especially preferred is ethylenediaminetetraacetic acid or salts thereof or citric acid or salts thereof. The amount is preferably 0.01 to 3%, especially 0.1 to 2% by weight of the dipping solution.

Among the setting systems mentioned above, the systems of kappa-carrageenan with cation and gellan gum with cation are specifically preferred. They produce high gel strength at low concentrations and have excellent compatibility with gelatin.

The Gelatins produced from the dipping solutions as described will consequently by a water content of 7 to 17% by weight contain by weight 83 to 93% gelatin, 0.01 to 10%, preferably 0.1 to 3% hydrocolloids, 0.001 to 3%, preferably 0.01 to 1% cations depending on the hydrocolloids used, and optional 0.001 to 3%, preferably 0.01 to 1% sequestering agents.

Capsules or films with the inventive gelatin composition may be manufactured with conventional machines by the conventional processes like extrusion moulding, injection moulding, casting or dip moulding.

The inventive gelatin composition may contain additionally acceptable plasticizers in an range from about 0 to 40% based upon the weight of the gelatin. Suitable plasticizers are polyethylene glycol, glycerol, sorbitol, sucrose, corn syryp, fructose, dioctyl-sodium sulfosuccinate, triethyl citrate, tributyl citrate, 1,2-propylenglycol, mono-, di- or triacetates of glycerol, natural gums or the like as well as mixtures thereof.

The inventive gelatin composition may contain in a further aspect additionally pharmaceutically or food acceptable coloring agents in the range of from 0 to 10% based upon the weight of the gelatin. The coloring agents may be selected from azo-, quinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

The shaped gelatin composition of the invention or the final product therof may be coated with a suitable coating agent like cellulose acetate phthalate, polyvinyl acetate phthalate, methacrylic acid gelatins, hypromellose phthalate, hydroxypropylmethyl cellulose phthalate, hydroxyalkyl methyl cellulose phthalates or mixtures thereof to provide e.g. enteric properties.

The gelatin composition of the invention may be used for the production of containers for providing unit dosage forms for example for agrochemicals, seeds, herbs, foodstuffs, dyestuffs, pharmaceuticals, flavoring agents and the like.

The inventive gelatin composition makes it useful for the encapsulation of caplets in a capsule, especially in a tamper-proof form. The encapsulation of a caplet in a capsule is preferred processed by cold shrinking together capsule parts, which are filled with a caplet, which comprises the steps providing empty capsule parts, filling at least one of said capsule parts with one or more caplets, putting said capsule parts together, and treating the combined capsule parts by cold shrinking.

The inventive gelatin composition is also useful for encapsulating and sealing the two capsule halves in a process in which one or more layers of the composition are applied over the seam of the cap and body, or by a liquid fusion process wherein the filled capsules are wetted with a hydroalcoholic solution that penetrates into the space where the cap overlaps the body, and then dried.

A specific embodiment of the instant invention is a hard gelatin capsule from fish gelatin filled with fish oil.

The improved properties of the gelatin composition are demonstrated by the following examples:

EXAMPLE 1

To 3.39 kg of deionised water is added 5 g of potassium acetate (0.10% by weight in the solution), followed by addition of 10 g kappa-carrageenan (0.20% by weight) under stirring at about 70° C. When a clear solution is obtained 1.60 kg of fish gelatin (32% by weight) are added at 60° C. under slow stirring until the gelatin is completely dissolved and the solution is defoamed.

The fish gelatin solution thus prepared is then poured into a dipping dish of a pilot machine of conventional hard gelatin capsule production equipment. While keeping the temperature of dipping fish gelatin solution at about 50° C., natural transparent hard fish gelatin capsules of size 1 were produced according to the conventional process with the same dimensional specifications to the conventional hard gelatin capsules.

EXAMPLE 2

To 5 kg of fish gelatin solution at 60° C., prepared according to example 1, are added 32.6 g of titanium dioxide previously dispersed into a small quantity of water. After homogenising the solution, it is poured into the dipping dish, and white opaque hard fish gelatin capsules of size 1 were produced as in the example 1.

The capsules from both examples have excellent dissolution properties as demonstrated in FIG. 1, showing the percentage of acetaminophen dissolved from capsules immersed in deionised water at 37° C. (USP XXIII) as a function of dissolution time.

What is claimed is:
1. A container for housing a unit dosage form of an active agent comprised of a gelatin composition comprising 83 to 93% by weight of fish gelatin, 7 to 17% by weight of water and 0.01 to 10% by weight of a hydrocolloid setting system containing one member selected from the group consisting of natural seaweeds, system containing one member selected from the group consisting of natural seaweeds, natural seed gums, natural plant exudates, natural fruit extracts, biosynthetic processed starch, cellulosic materials and polysaccharides, said hydrocolloid setting system providing the gelatin composition with gelling properties similar to non-fish gelatin containing gelatin compositions so that the gelatin compositions may be used to make hard gelatin capsules, wherein said container further comprises an enteric coating.

2. The container according to claim 1, wherein the enteric coating is made of at least one material selected from the group consisting of cellulose acetate phthalate, polyvinyl acetate phthalate, methacrylic acid gelatins, hypromellose phthalate, hydroxypropylmethyl cellulose phthalate, hydroxyalkyl methyl cellulose phthalates or mixtures thereof.

* * * * *